United States Patent [19]

Halm et al.

[11] Patent Number: 5,596,119
[45] Date of Patent: Jan. 21, 1997

[54] METHOD FOR CONTROLLING THE DIRECT PROCESS PRODUCT DISTRIBUTION

[75] Inventors: Roland L. Halm, Midland, Mich.; Charles S. Kuivila, Crestwood; Oliver K. Wilding, Lagrange, both of Ky.

[73] Assignee: Dow Corning Corporation, Midland, Mich.

[21] Appl. No.: 567,652

[22] Filed: Dec. 5, 1995

[51] Int. Cl.$^6$ ........................................... C07F 7/16
[52] U.S. Cl. ................................................... 556/472
[58] Field of Search ................................................ 556/472

[56] References Cited

U.S. PATENT DOCUMENTS

| | | | |
|---|---|---|---|
| Re. 33,452 | 11/1990 | Ward, III et al. | 556/472 |
| 2,380,995 | 8/1945 | Rochow et al. | 260/607 |
| 2,380,996 | 8/1945 | Rochow et al. | 260/607 |
| 4,602,101 | 7/1986 | Halm et al. | 556/472 |
| 4,973,725 | 11/1990 | Lewis et al. | 556/472 |
| 5,059,343 | 10/1991 | Halm et al. | 556/472 X |
| 5,281,739 | 1/1994 | Halm et al. | 556/472 |
| 5,312,948 | 5/1994 | Freeburne et al. | 556/472 |

*Primary Examiner*—Paul F. Shaver
*Attorney, Agent, or Firm*—William F. Boley

[57] ABSTRACT

A method for controlling the direct process to vary the concentrations of trialkylhalosilanes and alkyltrihalosilanes in the product. The method comprises contacting an alkyl chloride with silicon metalloid in the presence of a catalytic amount of a catalyst comprising 0.5 to 10 weight percent copper, 5 to 200 ppm tin, 25 to 2,500 ppm phosphorous, and greater than zero to less than 50 ppm zinc, where the concentration of each of the catalyst components is based on the weight of the silicon, at a temperature within a range of about 250° C. to 400° C. The present inventors have found that by controlling the zinc concentration the concentrations of trialkylhalosilanes and alkyltrihalosilanes in the product can be varied.

17 Claims, No Drawings

METHOD FOR CONTROLLING THE DIRECT PROCESS PRODUCT DISTRIBUTION

BACKGROUND OF INVENTION

The present invention is a method for controlling the direct process product distribution to vary the concentrations of trialkylhalosilanes and alkyltrihalosilanes in the product. The method comprises contacting an alkyl chloride with silicon metalloid in the presence of a catalytic amount of a catalyst comprising 0.5 to 10 weight percent copper, 5 to 200 ppm tin, 25 to 2,500 ppm phosphorous, and greater than zero to less than 50 ppm zinc, where the concentration of each of the catalyst components is based on the weight of the silicon, at a temperature within a range of about 250° C. to 400° C. The present inventors have found that by controlling the zinc concentration the concentrations of triatkylhalosilanes and alkyltrihalosilanes in the product can be varied. The present method is especially useful for increasing the concentration of trialkylhalosilane in the product.

The present invention relates to a modification of what is commonly referred to as the direct process for producing alkylhalosilanes, where the process comprises contacting an alkyl halide with particulate silicon in the presence of a copper catalyst. The process was first described by Rochow in U.S. Pat. No. 2,380,996 and U.S. Pat. No. 2,380,995.

Since the original description of the direct process by Rochow, the process has been refined and modified in numerous ways and is used for producing virtually all commercial alkylhalosilanes in the world today. When one considers that several million pounds of silanes are produced annually and consumed by the silicones commercial efforts, it is obvious that even small changes in the product distribution from the direct process can be important.

Commercially, the largest volume alkylhalosilane manufactured is dimethyldichlorosilane, as this alkylhalosilane constitutes the backbone of most high volume commercial silicone products after it has been hydrolyzed and condensed to form silicone polymers. Therefore, most efforts in optimizing the direct process have been directed toward obtaining the highest yield of dialkyldihalosilane. At times commercial demand for other alkylhalosilanes, particularly trialkylhalosilane, can exceed what is being produced in the direct process as optimized for production of dialkyldihalosilane. Current processes such as redistribution of dialkyldihalosilane to form trialkylhalosilane and alkyltrihalosilane are expensive to perform making then commercially unattractive. The present process provides a method for controlling the direct process to vary the concentration of trialkylhalosilane and alkyltrihalosilane in the product, thereby making the amounts of trialkylhalosilane and alkyltrihalosilane in the product more closely match commercial demand.

Ward et al., U.S. Pat. No. Re. 33,452, describe a process for making alkylhalosilanes by effecting reaction between an alkyl halide and powdered silicon in the presence of a copper-zinc-tin catalyst. Ward et al. suggest that improvements in reaction rate and product selectivity are achieved when copper is employed at a critical weight percent relative to silicon and critical weight ratios of tin and zinc are employed relative to copper. Ward et al. do not teach the presence of phosphorous or phosphorous compounds as part of the catalyst mixture.

Halm et al., U.S. Pat. No. 4,602,101, teach a method of controlling a process for the preparation of alkylhalosilanes from silicon and alkylhalides where phosphorous or phosphorous compounds are used as promoters to enhance selectivity of the process for dialkyldihalosilanes. Halm et al. teach that the catalyst can comprise 0.2 to 10 weight percent copper based on silicon present, 5 to 200 parts per million (ppm) tin, 25 to 2500 ppm phosphorous and optionally 100 to 10,000 ppm zinc.

Freeburne et al., U.S. Pat. No. 5,312,948, teach that a preferred catalyst for the reaction of silicon metalloid with an alkyl halide to form alkylhalosilanes comprises on an elemental basis by weight: 0.1 to 10 weight percent copper based on silicon present in the process, 50 to 10,000 ppm zinc, 5 to 200 ppm tin, and 25 to 2,500 ppm phosphorous.

The above described art does not teach conduct of the direct process in the presence of a catalyst mixture providing on an elemental basis by weight 0.1 to 10 weight percent copper, 5 to 200 ppm tin, 25 to 2,500 ppm phosphorous, and greater than zero to less than 50 ppm zinc, where the concentration of each of the catalyst components is based upon the weight of silicon in the process. Furthermore, the described art does not recognize that the concentration of zinc in the direct process can be controlled as a method of varying the concentration of trialkylhalosilane and alkyltrihalosilane in the product.

SUMMARY OF INVENTION

The present invention is a method for controlling the direct process to vary the concentrations of trialkylhalosilanes and alkyltrihalosilanes in the product. The method comprises contacting an alkyl chloride with silicon metalloid in the presence of a catalytic amount of a catalyst comprising 0.5 to 10 weight percent copper, 5 to 200 ppm tin, 25 to 2,500 ppm phosphorous, and greater than zero to less than 50 ppm zinc, where the concentration of each of the catalyst components is based on the weight of the silicon, at a temperature within a range of about 250° C. to 400° C. The present inventors have found that by controlling the zinc concentration the concentrations of trialkylhalosilanes and alkyltrihalosilanes in the product can be varied. The present method is especially useful for increasing the concentration of trialkylhalosilane in the product.

DESCRIPTION OF INVENTION

The present invention is a process for making alkylhalosilanes. The process comprises: contacting an alkyl halide with silicon metalloid in the presence of a catalyst comprising 0.5 to 10 weight percent copper, 5 to 200 ppm tin, 25 to 2,500 ppm phosphorous, and greater than zero to less than 50 ppm zinc, where the concentration of each of the catalyst components is based on the weight of the silicon, at a temperature within a range of about 250° C. to 400° C. In the preferred process the zinc concentration is controlled within the defined range as a means of varying the concentration of trialkylhalosilane and alkyltrihalosilane in the product.

Alkylhalosilanes that can be made by the present process are described by formula $$R_a H_b SiX_{4-a-b} \qquad (1).$$

In formula (1), each substituent R can be independently selected from a group consisting of alkyls comprising one to four carbon atoms. The substituent R can be, for example, methyl, ethyl, propyl, isopropyl, butyl, and tert-butyl. In formula (1), subscript a can have a value of zero, one, two, three, or four; subscript b can have a value of zero, one, or two; and the sum of terms a and b can be one, two, three, or four. In formula (1) the substituent X is a halogen. Preferred is when X is a chlorine atom. The preferred alkylhalosilanes are those in which subscript a has a value of one, two, or three and subscript b is zero. Also, preferred is where in formula (1) R is methyl and X is a chlorine atom. The most preferred alkylhalosilanes are trimethylchlorosilane, dimethyldichlorosilane, and methyltrichlorosilane.

In the present process an alkyl halide is contacted with silicon. Alkyl halides useful in the present process are described by formula $$RX, \qquad (2)$$

where R and X are as previously described. Preferred is where the substituent X of the alkyl halide is the chlorine atom. The preferred alkyl halide is methyl chloride.

The present process can be carried out as a batch process or continuous process in standard reactors for reacting silicon with alkyl halides. The process can be conducted, for example, in a fluidized-bed reactor, a stirred-bed reactor, or a vibrating-bed reactor.

It is preferred that contact of the alkyl halide with the silicon be effected in a fluidized-bed of particulate silicon. The process can be conducted in standard type reactors for reacting a fluidized-bed of particulates with a gas. The bed can be fluidized using the alkyl halide as the fluidizing media or using a mixture of the alkyl halide with a gas inert in the process as the fluidized media.

The silicon useful in the present process is any silicon having a purity of at least 95% by weight but less than 100% by weight of silicon. The preferred silicon is a metallurgical grade silicon having greater then about 98% but less than 100% by weight of silicon. The silicon can be a silicon copper alloy as described in Halm et al., U.S. Pat. No. 5,281,739, and incorporated by reference as an example of a useful silicon for the present process.

In the present process it is preferred that the silicon be a powder having an average particle size ranging from about 0.1 micron to 800 micron. A preferred average particle size for the silicon is within a range of about 0.1 to 150 microns. Even more preferred is a particulate silicon having a mass distribution characterized as described in Freeburne et al., U.S. Pat. No. 5,312,948, and incorporated by reference as an example of a preferred particulate silicon.

The present process is conducted in the presence of a catalyst comprising about 0.5 to 10 weight percent copper based on the weight of silicon present in the process, i.e. in the reaction mass. Preferred is when the catalyst comprises about 3 to 5 weight percent copper based on the weight of the silicon. The source of the copper added to the process may be, for example, powdered copper metal, powdered silicon-copper alloy, a compound of copper, or a mixture of two or more sources of copper. The copper compound may be, for example, cuprous chloride.

In the present process the catalyst must comprise 5 to 200 ppm tin based on the weight of the silicon present in the process. Preferred is when the catalyst comprises about 40 to 80 ppm tin based on the weight of the silicon. The source of the tin can be, for example, tin metal powder. The source of the tin can be, for example, a tin compound such as tin halides e.g. tetramethyltin, alkyl tin halides, and tin oxide.

In the present process the catalyst must include 25 to 2,500 ppm phosphorous based on the weight of the silicon present in the process. Preferred is when the catalyst comprises about 50 to 1,000 ppm phosphorous based on the weight of the silicon. The source of the phosphorous can be elemental phosphorous, metal phosphides, and compounds forming metal phosphides in the reaction mass of the process. Such sources of phosphorous are described in Halm et al., U.S. Pat. No. 4,602,101 which is hereby incorporated by reference. The source of phosphorous can be gaseous phosphorous compounds as described in Degen et al., U.S. Pat. No. 5,059,706, which is hereby incorporated by reference.

The present process must include greater than zero to less than 50 ppm zinc based on the weight of silicon present in the process. The source of the zinc can be for example, zinc metal, halides of zinc such as zinc chloride and zinc oxide. The source of the zinc can be an alloy such as brass.

The present inventors have unexpectedly found that varying the level of zinc within the process can provide a method for varying the amount of trialkylhalosilane and alkyltrihalosilane in the process mixture. The inventors have found that as zinc concentration is decreased the amount of trialkylhalosilane and alkyltrihalosilane in the reaction product is increased. Even more unexpected was the discovery that a disproportion increase in the trialkylhalosilane occurred in relation to the alkyltrihalosilane formed. Therefore, the present process is particularly useful for controlling the amount of alkyltrihalosilane formed in the process and for providing a reaction product enriched in the trialkylhalosilane.

The catalyst comprising the copper, tin, phosphorous, and zinc can be made by introducing the components into the reactor separately or as a mixture, masterbatch, alloy or blend of two or more of the components in elemental form or as compounds or mixtures thereof.

The present process can be conducted at a temperature within a range of about 250° C. to 400° C. The preferred temperature for conducting the process is within a range of about 260° C. to 320° C. Even more preferred is a temperature within a range of about 280° C. to 320° C.

The following examples are provided to illustrate the present invention. These examples are not intended to limit the scope of the claims herein.

Examples. The effect of varying the zinc concentration on methylchlorosilane product distribution was evaluated in a series of runs. The runs were made in a vibrating-bed type reactor similar to that described in Mass et al., U.S. Pat. No. 4,218,387. The reactor charges were prepared by combining 100 parts of refined, ground, metallurgical grade silicon with a catalyst package. The catalyst package comprised 6.5 parts cuprous chloride, 50 ppm tin, 2000 ppm copper phosphide comprising 14 weight percent phosphorous, and varying amounts of brass comprising 50 weight percent zinc, all concentrations based on the starting weight of silicon. The amount of zinc added for each run is described in Table 1. The silicon and catalysts package were mixed together by shaking. The charge was then placed in the reactor, which was closed and weighed to determine the initial weight. Nitrogen flow was initiated through the reactor and then the reactor heated to 315° C. by means of a heated fluidized sandbath. Methyl chloride gas was fed to the reactor for a total of 44 hours during which time all products and unreacted methyl chloride were collected in a cold-trap maintained below minus 40° C. Weight loss of the reactor was used as an indication of silicon conversion. The liquid collected in the cold-trap was analyzed by gas liquid chromatography (GLC) using a thermal conductivity (TC) detector. Reaction products detected by GLC-TC included dimethyldichlorosilane, trimethylchlorosilane, methyltrichlorosilane, and other chlorosilanes at concentrations below 1 weight percent. Yield of the reaction products were calculated as weight percentages of the total chlorosilanes detected in the cold trap. Nominal yields of methylchlorosilane products for each run were calculated by multiplying the concentrations of the individual methylchlorosilane (weight percent) in the total chlorosilane product collected in the cold trap by the average fractional silicon conversion. With the exception of run 1 data, each of the data entries in Table 1 is an average result measured for a pair of reactors run simultaneously.

TABLE 1

Effect of Zinc Concentration on Methylchlorosilane Products

| Run No. | Zinc (ppm) | Nominal Product Yields (%) | | |
|---|---|---|---|---|
| | | $Me_3SiCl$ | $MeSiCl_3$ | $Me_2SiCl_2$ |
| 1 | 300 | 1.5 | 3.0 | 78.8 |
| 2 | 90 | 2.1 | 3.5 | 78.1 |
| 3 | 50 | 2.7 | 4.4 | 76.3 |
| 4 | 25 | 2.9 | 4.5 | 76.7 |
| 5 | 0 | 3.0 | 5.0 | 75.1 |

We claim:

1. A process for making alkylhalosilanes, the process comprising:

contacting an alkyl halide with silicon metalloid in the presence of a catalyst comprising 0.5 to 10 weight percent copper, 5 to 200 ppm tin, 25 to 2,500 ppm phosphorous, and greater than zero to less than 50 ppm zinc, were the concentration of each of the catalyst components is based on the weight of the silicon, at a temperature within a range of about 250° C. to 400° C.

2. A process according to claim 1, where the alkyl halide is methyl chloride.

3. A process according to claim 1, where the catalyst comprises 3 to 5 weight percent copper, 40 to 80 ppm tin, 50 to 1000 ppm phosphorous, and greater than zero to less than 50 ppm zinc, where the concentration of each of the catalyst components is based on the weight of the silicon.

4. A process according to claim 1, where the temperature is within a range of about 260° C. to 320° C.

5. A process according to claim 1, where the temperature is within a range of about 280° C. to 320° C.

6. A process according to claim 1, where the catalyst is heat activated at a temperature within a range of about 270° C. to 350° C. prior to contact with the alkyl halide.

7. A process according to claim 1, where the alkyl halide is methyl chloride, the catalyst comprises 3 to 5 weight percent copper, 40 to 80 ppm tin, 50 to 1000 ppm phosphorous, and greater than zero to less than 50 ppm zinc, where the concentration of each of the catalyst components is based on the weight of the silicon, and the temperature is within a range of about 280° C. to 320° C.

8. A process for making an alkylhalosilane mixture with a controlled amount of trialkylhalosilane, the process comprising:

contacting an alkyl halide with silicon metalloid in the presence of a catalyst comprising 0.5 to 10 weight percent copper, 5 to 200 ppm tin, 25 to 2,500 ppm phosphorous, and zinc, where the concentration of each of the catalyst components is based on the weight of the silicon, at a temperature within a range of about 250° C. to 400° C.; where the concentration of the zinc is varied within a range of greater than zero to less than 50 ppm to control the concentration of the trialkylhalosilane in the alkylhalosilane mixture.

9. A process according to claim 8, where the alkyl halide is methyl chloride.

10. A process according to claim 8, where the catalyst comprises 3 to 5 weight percent copper, 40 to 80 ppm tin, 50 to 1000 ppm phosphorous, and greater than zero to less than 50 ppm zinc, where the concentration of each of the catalyst components is based on the weight of the silicon.

11. A process according to claim 8, where the temperature is within a range of about 260° C. to 320° C.

12. A process according to claim 8, where the temperature is within a range of about 260° C. to 320° C.

13. A process according to claim 8, where the catalyst is heat activated at a temperature within a range of about 270° C. to 350° C. prior to contact with the alkyl halide.

14. A process according to claim 8, where the alkyl halide is methyl chloride, the catalyst comprises 3 to 5 weight percent copper, 40 to 80 ppm tin, 50 to 1000 ppm phosphorous, and greater than zero to less than 50 ppm zinc, where the concentration of each of the catalyst components is based on the weight of the silicon, and the temperature is within a range of about 280° C. to 320° C.

15. A process for making a methylchlorosilane mixture with a controlled amount of trimethylchlorosilane, the process comprising in a fluidized-bed reactor contacting methyl chloride with silicon metalloid in the presence of a catalyst comprising 3 to 5 weight percent copper, 40 to 80 ppm tin, 50 to 1000 ppm phosphorous, and zinc, where the concentration of each of the catalyst components is based on the weight of the silicon, at a temperature within a range of about 280° C. to 320° C.; where the concentration of the zinc is varied within a range of greater than zero to less than 50 ppm to control the concentration of the trimethylchlorosilane in the methylchlorosilane mixture.

16. A process according to claim 1, where the catalyst comprises 50 to 1000 ppm phosphorous.

17. A process according to claim 1, where at least a portion of the zinc is added to the process as brass.

* * * * *